United States Patent
Lambrecht et al.

(10) Patent No.: US 6,391,365 B1
(45) Date of Patent: May 21, 2002

(54) USE OF 3,6-DIMETHYL-2(3H)-BENZOFURANONE AS FLAVOR MATERIAL AND NEW PROCESS FOR ITS PREPARATION

(75) Inventors: Stefan Lambrecht; Horst Surburg; Matthias Güntert; Volkmar Koppe, all of Holzminden (DE)

(73) Assignee: Haarman & Reimer GmbH, Holzminden (DE)

( * ) Notice: Subject to any disclaimer, the term of this patent is extended or adjusted under 35 U.S.C. 154(b) by 0 days.

(21) Appl. No.: 09/298,655

(22) Filed: Apr. 23, 1999

(30) Foreign Application Priority Data

Apr. 27, 1998 (DE) .......................... 198 18 731
Mar. 6, 1999 (DE) .......................... 199 09 980

(51) Int. Cl.⁷ ................. A23L 1/235; A61K 31/343; C07D 307/83
(52) U.S. Cl. ................. 426/536; 426/534; 514/470; 549/295; 549/302
(58) Field of Search ................. 549/295, 302; 514/470; 426/534, 536

(56) References Cited

U.S. PATENT DOCUMENTS 4,407,740 A * 10/1983 Kopsel et al. .............. 252/522

5,679,634 A * 10/1997 Vial et al. .............. 512/13

OTHER PUBLICATIONS

DN 128:294086, abstract Hintwerholzer et al, Flavour Fragrance J. 1998, 13(1), pp. 49–55, RN #57743–63–2.*

DN 127: 94493 abstract, Guth,H J. Agriculture Food Chem., 1997, vol. 45(8) pp. 3027–3032.*

Flavour and Fragrance Journal, Phenols and Lactones . . . ; Regula Naf et al pp. 203–208, Jan. 1998.*

Methodern der Org. Chemie, Houben–Weyl, 4th Ed. (month unavailable) 1981, vol. 5/2b b) aus cyclischen Verbindungen, Prof Dr. Maximilian Zander et al, pp. 107–129.

Tetrahedron, vol. 50, No. 4, (month unavailable) 1994, pp. 973–978, M.L.A. von Holleben et al A Selective Reduction of $\alpha,\beta$–Unsaturated Ketones.

* cited by examiner

Primary Examiner—Alan L. Rotman
Assistant Examiner—Rita Desai
(74) Attorney, Agent, or Firm—Joseph C. Gil; Noland J. Cheung

(57) ABSTRACT

3,6-Dimethyl-2(3H)-benzofuranone is a new, valuable flavor material. A process for its industrial-scale preparation was developed.

11 Claims, No Drawings

USE OF 3,6-DIMETHYL-2(3H)-BENZOFURANONE AS FLAVOR MATERIAL AND NEW PROCESS FOR ITS PREPARATION

FIELD OF THE INVENTION

The invention relates to flavours comprising 3,6-dimethyl-2(3H)-benzofuranone which have a lactone, coumarin and fruity note, to preparations comprising these flavours, such as foodstuffs, stimulants and oral hygiene products, and to a process for its preparation.

BACKGROUND OF THE INVENTION 3,6-Dimethyl-2(3H)-benzofuranone is known as an odoriferous substance for perfume compositions (WO 95/30667).

Also known are processes for the preparation of 3,6-dimethyl-2(3H)-benzofuranone which involve the use of chlorine-containing reagents and solvents which cause problems in use and make industrial-scale production difficult.

SUMMARY OF THE INVENTION

It has been found that 3,6-dimethyl-2(3H)-benzofuranone, of the formula

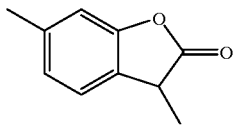

has in flavours advantages compared to known flavour materials.

Surprisingly, it emerged that this compound differs advantageously from known flavour materials by virtue of new, hitherto unknown flavour notes.

The flavours according to the invention are preferably present in liquid, spray-dried or encapsulated form.

DETAILED DESCRIPTION OF THE INVENTION

The chemical has a particularly intense flavour of coumarin, hay and coconut combined with a prolonged, noteworthy, complex flavour. This characteristic gains particular importance because coumarin itself must not be used as flavour material for the production of food flavours (EG Directive of Jun. 22, 1988). Moreover, the content of coumarin from natural sources (e.g. essential oils) is limited and maximum quantities are specified in foodstuffs. Compounds which have a coumarin-type flavour profile are therefore desirable flavour materials which can be used for imparting the sweet, lactone and hay notes which are typical of coumarin, without the use of coumarin itself.

According to the invention, the compound 3,6-dimethyl-2(3H)-benzofuranone is outstandingly suitable as flavour material for use in flavour compositions due to its outstanding organoleptic character and imparts a highly intense, natural note of coumarin and hay to the flavours in question. The fact that 3,6-dimethyl-2(3H)-benzofuranone causes a sweetness and complex flavour is also remarkable. In comparison with the lactones 5,6,7,7a-tetrahydro-3,6-dimethyl-2(4H)-benzofuranone and 5,6-dihydro-3,6-dimethyl-2(4H)-benzofuranone, which are already being used as flavour materials, the compound 3,6-dimethyl-2(3H)-benzofuranone has a more intensive flavour, i.e. the flavour manufactured using 3,6-dimethyl-2(3H)-benzofuranone has a more rapid, more noticeable and more potent impact ("impact effect") at comparable dosages.

The flavour quality of an flavour composition is thus considerably enhanced and improved by adding 3,6-dimethyl-2(3H)-benzofuranone, which, finally, leads to a comparatively higher acceptance of the finished products comprising such flavours.

The amount of the compound 3,6-dimethyl-2(3H)-benzofuranone in flavour compositions preferably amounts, according to the invention, ranges from 0.005 to 10% by weight, in particular 0.01 to 5% by weight, based on the total composition. Such flavour compositions can be used in the entire foodstuffs and stimulants sector and in oral hygiene products. They are particularly suitable for flavouring fatty compositions, baked foods, yoghurt, icecream, confectionery, chewing gum, alcoholic and soft drinks, tobacco, toothpaste and mouth washes. The dosage of such flavour compositions is preferably 0.0005 to 2% by weight, in particular 0.01 to 1% by weight, based on the finished foodstuff or stimulant.

Chemicals which do not only have the characteristic of imparting a particular flavour, but which have additional characteristics, have become increasingly important in the flavour and food industry. Examples of such additional characteristics may be specific stimuli which are conducted via the trigeminal nerve and are thus perceived. However, they may also be effects which inhibit, or enhance, olfactory and gustatory sensations.

One of the uses of the compound according to the invention focuses on its application in flavour compositions for confectionery, chewing gum and oral hygiene products (toothpaste, mouthwashes). In particular, they are used in mint compositions which are normally composed of peppermint oils (*Mentha piperita*), corn mint oils (*Mentha arvensis*) and/or spearmint oils (*Mentha spicata* and *Mentha cardiaca*) and their fractions with addition of synthetic and natural flavour materials and other natural extracts or essential oils. When used in foodstuffs and oral hygiene products, these mint flavours impart a minty flavour to them and impart a sensation of freshness in the mouth, and fresh breath. An important part of the flavour profile of peppermint oils (*Mentha piperita*) are the sweet hay notes (which some testers also term tobacco notes) which are particularly desired for flavouring confectionery and chewing gum. The flavour profile of a pure peppermint oil in chewing gum is given below and confirms this statement.

Flavour profile of a peppermint oil (*Mentha piperita*) in chewing gum (sugar-free, dosage 1.2%).

| Flavour profile | Intensity (1–10) |
|---|---|
| Impact | 6 |
| Complexity | 8 |
| Freshness | 6 |
| Coolness | 6 |
| Eucalyptus | 5 |
| Menthol | 5 |
| Menthone | 4 |
| Green | 2 |
| Spicy | 6 |
| Tea | 8 |
| Hay | 7 |
| Camomile | 5 |
| Floral | 4 |

-continued

| Flavour profile | Intensity (1–10) |
|---|---|
| Coumarin | 5 |
| Sweet | 7 |
| Soft | 8 |
| Earthy | 1 |
| Mushrooms | 1 |

Surprisingly, it has now been found that the compound 3,6-dimethyl-2(3H)-benzofuranone according to the invention can cause pronounced synergistic flavour effects. While its characteristics as an flavour material have the above-described flavour characteristics "coumarin, coconut, hay", it is also capable, in mint compositions, of significantly enhancing the "sweet" and "herbaceous" notes and to have a "balancing" effect.

These findings were determined in systematic organoleptic experiments on synthetic mint flavours in which the flavour material 3,6-dimethyl-2(3H)-benzofuranone according to the invention was either added or left out of the composition. Conventional concentrations (1–1.5%) of the mint flavours were incorporated into chewing gum bases with and without sugar and tasted after approximately 4 weeks' storage. A comparison of the mint flavours with and without 3,6-dimethyl-2(3H)-benzofuranone resulted in the finding that the compound according to the invention has a synergistic effect and, in particular, "enhances the sweetness, enhances the herbaceousness, enhances the impact and has a generally balancing effect". The organoleptic chewing experiments were carried out over up to 30 minutes.

The experiments on oral hygiene products were carried out in particular on toothpastes. Both calcium carbonate and silicate bases were used. The bases were sweetened with 0.2% of saccharin. Again, synthetic mint flavours in which the flavour material 3,6-dimethyl-2(3H)-benzofuranone according to the invention was either added or left out of the composition were employed. The comparison of the mint flavours with and without 3,6-dimethyl-2(3H)-benzofuranone led to the result that the compound according to the invention acts as a synergist and, in particular, "enhances the impact, enhances the sweetness, masks the sharpness of the menthol and is generally balancing".

In summary, it can be said that the compound 3,6-dimethyl-2(3H)-benzofuranone according to the invention in mint compositions in chewing gum has the following synergistic flavour characteristics:

enhances sweetness enhances herbaceousness enhances impact balances the overall composition.

The compound 3,6-dimethyl-2(3H)-benzofuranone has the following synergistic flavour characteristics in mint compositions in toothpaste:

enhances impact enhances sweetness balances menthol sharpness balances the overall composition The mint flavours comprising the flavour material 3,6-dimethyl-2(3H)-benzofuranone according to the invention which are used can be employed in liquid and in dry form. In liquid form, they are employed in a customary solvent such as ethanol, propylene glycol or triacetin, while the dry flavours are obtained by spray-drying or by encapsulation by one of the processes conventionally used in the flavour industry. These are, in particular, extrusion and spray granulation.

The preparation of aromatic compounds from saturated and partially saturated precursors by catalytic dehydrogenation is an organochemical procedure known per se (Methoden der Org. Chemie, Houben-Weyl, 4th Ed. 1981, Vol. 5/2b). The use of ($\alpha,\beta$-unsaturated carbonyl compounds as hydrogen acceptor has also been described (M. L. A. von Holleben, M. Zucolotto, C. A. Zini, E. R. Oliveira, Tetrahedron, 1994, 50, 973–978). However, this method has not been used to date for the preparation of 2(3H)-benzofuranones from corresponding partially hydrogenated precursors.

However, in the case of 3,6-dimethyl-2(3H)-benzofuranone, such a process has the advantage that a starting material which is available on an industrial scale exists in the form of 5,6-dihydro-3,6-dimethyl-2(4H)-benzofuranone (DE 3.017.068).

It has been found that 3,6-dimethyl-2(3H)-benzofuranone is successfully prepared by carrying out the dehydrogenation reaction in the liquid phase, the dehydrogenation catalyst used being a metal of sub-group 8 and the hydrogen acceptors used being ($\alpha,\beta$-unsaturated carbonyl compounds.

Palladium fixed to a support is preferably used as dehydrogenation catalyst. The support is preferably charcoal.

Hydrogen acceptors which can be used are compounds such as fumaric esters, maleic esters, mesityl oxide, benzalacetone, isophorone, verbenone, crotonic esters and the like. The use of dehydrogenating agents whose boiling point is such that the product boils either considerably later (for example mesityl oxide) or considerably earlier (for example dibutyl maleate) is particularly preferred. This allows simple distillation.

The $\alpha,\beta$-unsaturated carbonyl compounds can be employed in an excess and therefore simultaneously act as solvents. The use of a further solvent can therefore be dispensed with.

The reaction proceeds at temperatures between 70 and 250° C.; in the case of mesityl oxide, the process is preferably carried out under reflux conditions at approx. 130° C. When using dibutyl maleate, the process is preferably carried out at 170° C. The process may be carried out under atmospheric pressure or under super- or subatmospheric pressure.

The amount of catalyst may be 0.001 to 30%, preferably at 0.2 to 15%.

EXAMPLES

Example 1

Preparation of 3,6-dimethyl-2(3H)-benzofuranone using Mesityl Oxide as Hydrogen Acceptor A mixture of 100 g of 5,6-dihydro-3,6-dimethyl-2(4H)-benzofuranone, 500 ml of mesityl oxide and 10 g of palladium-on-charcoal, 5% by weight, is heated for two hours under reflux. The 3,6-dimethyl-2(3H)-benzofuranone to 5,6,7,7a-tetrahydro-3,6-dimethyl-2(4H)-benzofuranone ratio of approx. 3:1 is subsequently determined by gas chromatography.

The reaction mixture was composed as follows:

Mesityl oxide: 69.7%

3,6-Dimethyl-2(3H)-benzofuranone 14.7%

5,6,7,7a-Tetrahydro-3,6-dimethyl-2(4H)-benzofuranone: 4.6%

To purify the product, the mesityl oxide was distilled off using a 20 cm packed column and the residue was fractionated. At a b.p. of 110° at 3 mbar, approx. 80 g of a fraction composed of 3,6-dimethyl-2(3H)-benzofuranone and 5,6,7,7a-tetrahydro-3,6-dimethyl-2(4H)-benzofuranone was collected, from which pure 3,6-dimethyl-2(3H)-benzofuranone was obtained by precision distillation using a Spaltrohrkolonne®.

Spectroscopic data (FT/IR):

| | |
|---|---|
| 2979 cm$^{-1}$ | w |
| 1801 cm$^{-1}$ | s |
| 1632 cm$^{-1}$ | m |
| 1501 cm$^{-1}$ | m |
| 1454 cm$^{-1}$ | m |
| 1423 cm$^{-1}$ | m |
| 1096 cm$^{-1}$ | m |
| 1030 cm$^{-1}$ | m |
| 994 cm$^{-1}$ | m |
| 943 cm$^{-1}$ | m |

Example 2

Preparation of 3,6-dimethyl-2(3H)-benzofuranone by Means of Dehydrogenation Using Dibutyl Maleate as Hydrogen Acceptor A mixture of 1000 g of 5,6-dihydro-3,6-dimethyl-2(4H)-benzofuranone, 2000 ml of dibutyl maleate and 50 g of palladium-on-charcoal, 5% by weight, was heated for approx. 3 hours at 170° C. in an autoclave under autogenous pressure. After filtration, the product was purified by fractionating on an 80 cm packed column. Approx. 735 g of pure 3,6-dimethyl-2(3H)-benzofuranone were obtained at a b.p. of approx. 90° C. at 1 mbar.

Example 3

Preparation of a Coconut Flavour

The following were mixed (all in g):

| | |
|---|---|
| Acetylmethylcarbinol | 5.0 |
| γ-Nonalactone | 50.0 |
| Benzaldehyde | 0.5 |
| Capric acid | 5.0 |
| Vanillin | 5.0 |
| 1,2-Propylene glycol | 934.5 |
| Total | 1000.0 |

If 0.5 g of the propylene glycol was replaced by 0.5 g of 3,6-dimethyl-2(3H)-benzofuranone, the flavour was shifted markedly towards a typical coconut flavour and gained considerably in sweetness, complexity and impact.

Example 4

Preparation of a Peppermint Flavour

The following were mixed (all in g):

| | |
|---|---|
| Eucalyptol | 50 |
| 1-Limonene | 20 |
| Menthofuran | 20 |
| 1-Menthol | 450 |
| Menthone/Isomenthone | 250 |
| 1-Menthyl acetate | 40 |
| Alcohol, 96% v/v | 170 |
| Total | 1000 |

If 1 g of the alcohol was replaced by 1 g of 3,6-dimethyl-2(3H)-benzofuranone, the flavour was markedly sweeter, had greater lactone and coumarin character and gained in complexity and impact. A more balanced flavour was also observed.

What is claimed is:

1. A method of flavoring food comprising compositions which comprise 3,6-dimethyl-2(3H)-benzofuranone.

2. A method of flavoring food according to claim 1, wherein the 3,6-dimethyl-2(3H)-benzofuranone content is between 0.005 and 10% by weight based on the total composition.

3. A method of flavoring food according to claim 1, wherein the 3,6-dimethyl-2(3H)-benzofuranone content is between 0.01 and 5% by weight based on the total composition.

4. A method of flavoring food according to claim 1, wherein said food is a fatty composition, baked food, yogurt, ice cream, confectionary product, chewing gum, alcoholic or soft drink.

5. A method of flavoring food according to claim 1, wherein the content of compositions comprising 3,6-dimethyl-2(3H)-benzofuranone is 0.0005 to 2% by weight based on the finished food product.

6. A method of flavoring food according to claim 1, wherein the content of compositions comprising 3,6-dimethyl-2(3H)-benzofuranone is 0.01 to 1% by weight based on the finished food.

7. A method of flavoring oral hygiene products comprising a composition which comprises 3,6-dimethyl-2(3H)-benzofuranone wherein said oral hygiene product is toothpaste or mouthwash.

8. A method of flavoring oral hygiene products according to claim 7, wherein the content of said composition comprising 3,6-dimethyl-2(3H)-benzofuranone is 0.0005 to 2% by weight based on the finished oral hygiene product.

9. A method of flavoring oral hygiene products according to claim 8, wherein the content of said composition comprising 3,6 dimethyl-2(3H)-benzofuranone is 0.01 to 1% by weight based on the finished oral hygiene product.

10. A process for the preparation of 3,6-dimethyl-2(3H)-benzofuranone, wherein 5,6-dihydro-3,6-dimethyl-2(4H)-benzofuranone is subjected to catalytic dehydrogenation.

11. A method for flavoring a tobacco product comprising compositions which comprise 3,6-dimethyl-2(3H)-benzofuranone.

* * * * *